United States Patent
Costantini et al.

(10) Patent No.: US 6,787,669 B1
(45) Date of Patent: Sep. 7, 2004

(54) METHOD FOR SEPARATING AND PURIFYING ADIPIC ACID

(75) Inventors: Michel Costantini, Lyons (FR); Eric Fache, Caluire et Cutre (FR); Philippe Leconte, Meyzieu (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/623,414

(22) PCT Filed: Feb. 24, 1999

(86) PCT No.: PCT/FR99/00420

§ 371 (c)(1),
(2), (4) Date: Nov. 8, 2000

(87) PCT Pub. No.: WO99/44980

PCT Pub. Date: Sep. 10, 1999

(30) Foreign Application Priority Data

Mar. 5, 1998 (FR) .......................... 98 02928

(51) Int. Cl.$^7$ .............................. C07C 51/31
(52) U.S. Cl. ....................................... 562/543
(58) Field of Search ........................ 562/543

(56) References Cited

U.S. PATENT DOCUMENTS

| | | | |
|---|---|---|---|
| 3,933,930 A | | 1/1976 | Dougherty et al. |
| 5,463,119 A | * | 10/1995 | Kollar |
| 5,900,506 A | * | 5/1999 | Fache et al. |

FOREIGN PATENT DOCUMENTS

| | | |
|---|---|---|
| DE | 764 488 | 6/1953 |
| DE | 44 28 977 | 2/1994 |
| FR | 1 266 886 | 11/1961 |
| FR | 2 092 524 | 1/1972 |
| FR | 2 353 513 | 12/1977 |
| FR | 2 390 415 | 12/1978 |
| FR | 2 757 155 | 6/1998 |
| WO | 96 03365 | 2/1996 |
| WO | 97 36673 | 10/1997 |

OTHER PUBLICATIONS

Derwent abstract (Acc No 1973–51168U) of JP 81006975B (1981). Enhanced purity adipic acid production.*
Derwent abstract (Acc No 1973–31683U) of JP 73016902 (1973). Adipic acid purification—by contact with ozone containing gas and crystallization.*
Derwent abstract (Acc. No. 1980–24322C) of JP 55024153 (1980). Recovery of high purity adipic acid.*
Derwent abstract (Acc No 1977–86545Y) of BE 855237A (1977). Purification of adipic acid.*
Derwent abstract (Acc No 1971–07345S) of JP 71002802B (1971). Adipic acid purification.*

* cited by examiner

Primary Examiner—Ralph Gitomer
(74) Attorney, Agent, or Firm—Burns, Doane, Swecker & Mathis, L.L.P.

(57) ABSTRACT

The present invention relates to the treatment of the reaction mixtures resulting from an oxidation reaction of cyclohexane to adipic acid and more particlarly to the separation of the various constituents of the said mixtures and to the purification of the adipic acid.

22 Claims, No Drawings

METHOD FOR SEPARATING AND PURIFYING ADIPIC ACID

This application was filed as a 371 application based on application PCT/FR99/00420 filed Feb. 24, 1999 which claims priority to application FR98/02928 filed Mar. 5, 1998.

The present invention relates to the treatment of the reaction mixtures resulting from an oxidation reaction of cyclohexane to adipic acid and more particularly to the separation of the various constituents of the said mixtures and to the purification of the adipic acid.

The direct oxidation of cyclohexane to adipic acid is a process which has been operated for a long time, in particular because of the obvious advantages which there would be in converting cyclohexane to adipic acid in a single stage and without employing an oxidizing agent, such as nitric acid, this compound generating nitrogen oxides which would subsequently have to be treated in order to prevent any pollution.

Patent WO-A-94/07834 discloses the oxidation of cyclic hydrocarbons to corresponding diacids, in the liquid phase comprising a solvent, using a gas comprising oxygen in the presence of an oxidation catalyst, such as a cobalt compound, the said solvent comprising an organic acid having only primary or secondary hydrogen atoms. This patent enlarges more particularly on the stages of treatment of the final reaction mixture. This treatment consists in separating the diacid formed, by cooling the mixture in order to bring about the precipitation of the said diacid, and in separating, by filtration, the diacid from two liquid phases, a non-polar phase, which is recycled, and a polar phase, which is also recycled after optional hydrolysis and separation of an additional amount of diacid.

This patent provides a solution for oxidizing cyclohexane to adipic acid in one stage with an industrially acceptable selectivity but it does not furnish an industrially applicable solution to the treatment of the reaction mixture resulting from the oxidation, taking into account the separation of the various reaction products and byproducts, unconverted materials and catalyst.

In addition, it turns out in practice that such a perfunctory treatment process does not result in an adipic acid exhibiting the purity required in a great many applications of this highly important starting material.

This is because, whether for the production of polyamide 6,6 or for other applications, such as the production of some polyurethanes, the purity of the adipic acid employed must be extremely high, both for contents of organic byproducts, which can result in undesiable colourations, and for contents of metal residues, in particular traces of the catalyst used.

The present invention thus relates to an improved process for the treatment of the reaction mixture resulting from the direct oxidation of cyclohexane to adipic acid by molecular oxygen in an organic solvent in the presence of a catalyst. characterized in that the said process comprises:

a separation into two liquid phases by settling: an upper phase, which essentially cyclohexane, and a lower phase, essentially comprising the solvent, the diacids formed, the catalyst and a portion of the other reaction products and of the unconverted cyclohexane;

a distillation of the said lower phase, making it possible to separate, on the one hand, a distillate comprising at least a portion of the most volatile compounds, such as the organic solvent and water, as well as unconverted cyclohexane, cyclohexanone, cyclohexanol, cyclohexyl esters and lactones possibly present, and, on the other hand, the distillation bottoms comprising the diacids formed and the catalyst;

a separation of the catalyst from the distillation bottoms obtained above, either by crystallization from water, by electrodialysis or by passing over an ion-exchange resin, after dissolution of the said distillation bottoms in water, or alternatively by washing with water or by liquid-liquid extraction;

a reducing and/or oxidizing purification treatment ot the adipic acid in aqueous solution;

a crystallization, preceding or following the purification treatment, when the crystallization has not been carried out in order to separate the catalyst;

a recrystallization of the adipic acid from water.

The cyclohexane phase obtained in the stage of separation by settling is generally reintroduced into a cyclohexane oxidation operation.

The organic solvent employed in the oxidartion of cyclohexane is more particularly chosen from aliphatic carboxylic acids. It is generally acetic acid.

The catalyst preferably comprises cobalt, manganese or a mixture of cobalt with one or more other metals, such as manganese, chromium, iron, zirconium, hafnium or copper. Among cobalt-based mixtures, catalysts comprising either cobalt and chromium, or cobalt, chromium and zirconium, or cobalt and iron, or cobalt and manganese, or cobalt andzirconium and/or hafnium are more particularly well suited. This catalyst is used for the oxidation of cyclohexane in the form of compounds of these metals which are soluble in the reaction mixture.

The stage of distillation of the lower phase is carried out so that most, insofar as possible virtually all, of the unconverted cyclohexane which may still be present in this lower phase and of the solvent, in particular of the carboxylic acid preferably used, is separated from the adipic acid. This stage makes it possible co separate the light organic compounds (more volatile than the diacids), which it is advantageous to recycle in the stage of oxidation of cyclohexane, optionally after a treatment intended to remove water from them. Mention may be made, as examples of such light organic compounds, of adipogenic compounds (capable of being converted into adipic acid), such as cyclohexanol, cyclohexanone or cyclohexyl acetate, and other compounds, such as lactones (essentially butyrolactone and valerolactone).

The distillation stage is generally carried out at a temperature of 25° C. to 250° C. and under an absolute pressure of between 10 Pa and atmospheric pressure. The temperature of the mixture during the distillation will preferably be maintained between 70° C. and 150° C.

The distillation can, if necessary, be carried out in several successive stages, in particular in the preferred form, where it is desired to remove the largest portion, for example more than 90% and even more than 99%, of the solvent, such as an aliphatic carboxylic acid.

To perfect the separation of the light organic compounds mentioned above, use may be made, in the distillation, of an inert entrainer which can either be water in the form of steam or also be an inert gas, such as nitrogen.

The distillation stage can optionally be completed by an extraction of the distillation bottoms using a waterimmiscible organic solvent. This extraction can be used to separate the esters, in particular cyclohexyl esters, which can be found in the distillation bottoms. Use may be made, as non-limiting example of such organic solvents, of aliphatic, cycloaliphatic or aromatic hydrocarbons, aliphatic, cycloaliphatic or aromatic carboxylic acid esters, or ketones. As it is preferable to avoid as far as possible the introduction of new compounds into the process of the invention, cyclohexane will advantageously be used as extraction solvent. The extract can be recycled in a new oxidation reaction, either directly or after hydrolysis of the esters.

The distillate obtained in the distillation operation described above comprises the various volatile compounds and water. These volatile compounds are of economic value and are thus recycled in a new oxidation reaction of cyclohexane, after an at least partial removal of the water by any known means, in particular by azeotropic distillation.

The distillation bottoms obtained at the end of the distillation, which have, if appropriate, been subjected to the extraction operation, are treated in order to separate the catalyst which they comprise.

This separation can be carried cut, in a first alternative form, by a crystallization process which consists essentially in dissolving the said distillation bottoms in the minimum amount of water, generally while hot, and then crystallizing mainly the adipic acid. Furthermore, the aqueous solution comprising the catalyst can be treated in ortder to isolate the said catalyst, which can be recycled in a new oxidation operation.

The separation can also be carried out by other known techniques, for example, after dissolution out an electrodialysis of the solution obtained or by passing the said solution over an ion-exchange resin. The electrodialysis can be carried out as disclosed in Patent Application WO-A-97/36673. The ion-exchange resins are resins capable of binding the metal cations of the catalyst. They generally have functional groups of an acidic nature or functional groups of a complexing nature. The functional groups of an acidic nature are generally sulphonic acid or carboxylic acid groups. The functional groups of a complexing nature are generally groups of imidodiacetic or aminophosphonic type.

The separation can also be carried out, in another alternative form, by one or more washing operations on the distillation bottoms with water. By such a washing operation, the catalyst, in particular, as well as a portion of the diacids, in particuiar glutaric acid and, to a lesser extent, succinic acid, are dissolved. In order to prevent or greatly restrict the dissolution of adipic acid, use is made of an amount of water or of water saturated with adipic acid which represents, by weight, from 1% to 100% of the weight of the distillation bottoms and preferably from 10% to 50%.

The stage of separation of the catalyst is followed by an operation of purification of the adipic acid, which has seen placed in aqueous solution.

This purification can be carried out by hydrogenation and/or by treatment with nitric acid and/or by oxidation with molecular oxygen or with any other oxidizing agent, such as ozone and hydroperoxides (including hydrogen peroxide).

The hydrogenation is advantageously carried out using hydrogen in the presence of a catalyst. Mention may be made, as catalyst, as non-limiting examples, of those which comprise at least one metal from group VIII of the Periodic Classification of the Elements, such as palladium, platinum, ruthenium, osmium, rhodium, iridium, nickel or cobalt. These metals are preferably in metallic form and are advantageously deposited on a solid support. Use may non-limitingly be made, as solid support, of charcoals, clays, zeolites or oxides, such as silicas, aluminas, silicas aluminas or magnesia. The catalyst can be employed as a stationary bed or as a fluidized or moving bed. The hydrogenation can be carried out continuously or batchwise but continuous operation is favoured from the viewpoint of a plant of industrial type.

The treatment with nitric acid can be carried out with an aqueous solution generally comprising from 20% to 80% of pure nitric acid by weight per weight of solution. This treatment is generally carried out by heating the mixture at a temperature of 25° C. to 120° C. and preferably of 40° C. to 100° C. for a period of time of a few minutes to a few hours. The heating can advantageously be carried out via successive stationary phases at a temperature situated in the ranges of values indicated above. The amount of nitric acid employed can vary widely. It must, on the one hand, very clearly be sufficient for the desired oxidation and, on the other hand, not be excessively high, for both technical and economic reasons. Use will generally be made of 0.8 mol to 4 mol and preferably of 1 mol to 2 mol of nitric acid per 100 grams of adipic acid solution to be treated. This treatment is generally carried out in the absence of catalyst. It can also be carried out in the presence of a catalyst comprising one or more cobalt, copper and/or vanadium compounds. As the treatment can result in the formation of nitrous vapours, it is preferably completed by the removal, while hot, of the said nitrous vapours formed by movement through the liquid mixture of an inert gas, such as nitrogen.

The oxidation with molecular oxygen is more particularly carried out with air, air enriched in oxygen or air depleted in oxygen, in the presence of a catalyst. The catalysts described above for the treatment by hydrogenation are suitable for this treatment with molecular oxygen. Use is preferably made of a metal chosen from palladium, platinum, ruthenium, osmium, rhodium or iridium.

The oxidation with hydroperoxides, preferably carried out with hydrogen peroxide, can be uncatalysed or can be catalysed by the catalysts conventionally used with this type of oxidizing agent. Preference is more particularly given to heterogeneous catalysts of molecular sieve type. Reference may be made, for example, to the catalysts disclosed in Patent Application WO 96/31455 or in Patent FR-A-2,744,719. In particular, use may advantageously be made of those which comprise titanium.

The purification by hydrogenation and/or nitric treatment and/or oxidation using molecular oxygen, ozone or hydroperoxide can be preceded or followed by a treatment for adsorption of impurities by finely divided solid, such as, for example, a carbon black or an alumina. This treatment schematically comprises the addition of carbon black or of alumina to the hot aqueous solution comprising the adipic acid and the filtration while hot of the said solution in order to separate the carbon black and the adsorbed impurities. This treatment can also be carried out continuously on a stationary bed.

The treatment by hydrogenation and/or the treatment with nitric acid and/or the treatment by oxidation using molecular oxygen, ozone or hydroperoxide is generally followed by an operation of crystallization of the adipic acid from water, which makes it possible in particular to separate the glutaric and succinic acids present, and then by recrystallization of the said adipic acid in order to achieve the desired purity. When the separation of the catalyst has been carried out using a crystallization, it is usually sufficient to carry out a recrystallization.

This crystallization and/or this recrystallization can be carried out under the conditions described above. They essentially consist in dissolving the adipic acid in the minimum amount of water, generally while hot, and in then crystallizing or recrystallizing the said adipic acid by cooling the solution under the usual crystallization conditions (for example, programmed gradual decrease in the temperature, seeding with adipic acid crystals, if appropriate).

The examples which follow illustrate the invention.

EXAMPLES 1 AND 2

The following are charged at room temperature to a 1.5 liter autoclave, purged beforehand with nitrogen, which is lined with titanium and equipped with a six-bladed turbine impeller and with various openings for the introduction of the reactants and fluids or for the discharge of the reaction products and fluids:

cobalt acecate tetrahydrate: 4.0 g (16 mmol)

acetic acid: 357 g (5.95 mol)

cyclohexane: 292.5 g (3.48 mol)

cyclohexanone: 3.2 g (32.7 mmol).

After closing the autoclave, the nitrogen pressure is brought to 20 bar, stirring is started at 1000 revolutions/min and the temperature is brought to 105° C. over 20 min. The nitrogen is then replaced with 20 bar of depleted air (5% oxygen). The gas flow rate at the inlet is adjusted to 250 liters/hour.

After an induction period of approximately 10 min, during which there is no consumption of oxygen, the temperature rises by 2 to 3° C. and the oxygen begins to be consumed. The oxygen assay in the air at the inlet of the autoclave is gradually brought to 21% according to the consumption by the oxidation.

The oxygen assay at the outlet of the reactor remains below 5% throughout the test. The temperature in the autoclave oscillates between 104.9 and 105.1° C.

When 50 liters of oxygen have been consumed (degree of conversion of the cyclohexane of approximately 20%), the continuous injection of the liquid phase is begun: the injection of an acetic acid solution comprising 1.1% by weight of cobalt acetate tetrahydrate at a flow rate of 3.7 ml/min and injection of cyclohexane at a flow rate of 4.1 ml/min. The liquid product is stored continuously in a 7 liter decanter at 70° C.

After 400 minutes since the beginning of the recaion, the air is gradually replaced by nitrogen and the contents of the autoclave are transferred to the decanted. The contents of the decanter are a two-phase mixture. The upper phase, which is essentially cyclohexane and contains few products and little cobalt, is separated. The lower acetic phase (2340 g) comprises the bulk of the oxidation products and of the cobalt. The acetic phase is subjected to a two-stage distillation under the following conditions:

a) Distillation Stage 1:

pressure: 60 kPa temperature: 135° C.

The results obtained are collated in the table below.

The distillate represents 1830 g and the distillation bottoms approximately 510 g.

b) Distillation Stage 2.

The distillation bottoms resulting from the stage 1) are freed from the volatile organic compounds whicn they comprise by virtue of injection of steam at 150° C. under a pressure 10 kPa (743 g of steam over 7 h).

The results obtained are collated in the table below.

| Compounds | Starting untreated mass | Distillation bottoms, stage 1 | Distillation bottoms, stage 2 |
| --- | --- | --- | --- |
| cyclo-hexanone | 183.3 mmol | 75 mmol | 0 |
| cyclohexyl acetate | 19.3 mmol | 36.3 mmol | 0 |
| free cyclohexanol | 217.3 mmol | 56.5 mmol | 0 |
| glutaric acid* | 184.5 mmol | 184.5 mmol | 184.6 mmol |
| succinic acid* | 121.1 mmol | 121.1 mmol | 121.1 mmol |
| adipic acid* | 1656.5 mmol | 1656.5 mmol | 1656.5 mmol |
| hydroxy-caproic acid | 23.4 mmol | 23 mmol | 23 mmol |
| hydroxy-adipic acid | 76 mmol | 76 mmol | 76 mmol |
| butyro-lactone | 77.9 mmol | 64 mmol | 0 |
| valerolactone | 23.4 mmol | 10 mmol | 0 |
| acetic acid | 1830 g | not quantitatively determined | <10 mmol |

(*): total acid (free and esterified)

1000 g of water are added to the distillation bottoms from the stage 2. The combined mixure is heated to 70° C. and is then gradually cooled to room temperature according to the following temperature profile: 12° C./h from 70° C. to 60° C., 5° C./h from 60° C. to 55° C., 11° C./h from 55° C. to 44° C., 24° C./h from 44° C. to 20° C.

After filtration and washing operations with water, 200 g of crude adipic acid are obtained, which acid has a mean particle size of 300 µm and comprises (as weight per weight):

succinic acid: 0.2000% glutaric acid: 0.0030% cobalt: 0.0100%.

A recrystallization from water of 65 g of this crude adipic acid results in an adipic acid (A) having a mean particle size of 300 µm comprising (as weight per weight):

succinic acid: 0.0002% glutaric acid: <0.0001% cobalt: <0.0002%.

The cobalt catalyst is found in the aqueous crystallization liquors.

65 g of the crude adipic acid are subjected to the following treatment by hydrogenation.

65 g of crude adipic acid obtained above from the distillation bottoms from the stage 2, 152 g of water and 2.8 g of a Pd/C catalyst comprising 10% by weight of Pd are introduced into a 500 ml autoclave which is agitated by being rocked and which is heated with an electric oven. After having purged the autoclave at room temperature with nitrogen, it is pressurized to 20 bar with hydrogen.

Heating is carried out at 135° C. for 2 h. Cooling is carried out to 70° C., depressurization is carried out with care and the catalyst is filtered off at this temperature. The adipic acid is subsequently recrystallized as above for the acid (A). A purified adipic acid (B) is thus obtained which exhibits characteristics very similar to the adipic acid (A) as regards succinic acid, glutaric acid and cobalt.

65 g of the crude adipic acid are subjected to the following nitric treatment.

158 g of 52% by weight nitric acid are heated to 65° C. 32 g of the crude adipic acid obtained above from the distillation bottoms from the stage 2 are added over 10 min.

70 mg of sodium nitrite are then added. The temperature rises to 75° C. While maintaining this temperature, 33 g of the crude acid obtained in the distillation bottoms from the stage 2 are added over 10 min. The reaction mixture is maintained at this temperature for 1 h and then the nitrous vapours formed are removed by bubbling in nitrogen for 30 min.

The adipic acid is subsequently recrystallized as above for the acid (A) and then washing is carried out with water until the wash liquors are neatral. A purified adipic acid (C) is thus obtained which exhibits very similar characteristics to the adipic acid (A) as regards succinic acid, glutaric acid and cobalt.

Batches (A), (B) and (C) of adipic acid are subjected to a heating test. This test consists in heating 50 g of each batch at 215° C. for 205 min and in then placing each of them in 415 ml of a 5% aqueous ammonium solution.

The absorbance at 454 nm (yellow region) of the ammonium adipates obtained is susequently measure.

The following results, expressed as relative absorbance, are obtained, the reference adipic acid (A) representing the value 1:

adioic acid (A): 1
adipic acid (B): 0.0.8
adipic acid (C): 0.12.

The adipic acids (B) and (C) purified according to the present invention are markedly less coloured than the adipic acid (A) not comprised within the invention. The absorbance at 454 nm is respectively 12 and 8 times lower for (B) and (C) than for (A), which, however, already possesses an excellent purity with respect to the lower diacids or to the catalyst (Co) but which proves to comprise more significant traces of other coloured impurities.

What is claimed is:

1. A process for treating the reaction mixture resulting from the direct oxidation of cyclohexane to adipic acid with molecular oxygen in an organic solvent in the presence of a catalyst, said process comprising:
   (a) separating the reaction mixture into two liquid phases by settling to form an upper phase comprising cyclohexane, and a lower phase comprising an organic solvent, diacids formed during the oxidation reaction, a catalyst and a portion of other reaction products and unconverted cyclohexane:
   (b) distilling said lower phase to provide (i) a distillate comprising at least a portion of the most volatile compounds and (ii) a distillation bottoms comprising the diacids formed and the catalyst;
   (c) separating the catalyst from the distillation bottoms;
   (d) purifying the adipic acid in an aqueous solution, said purifying step consisting essentially of a reducing and/or an oxidizing purification treatment;
   (e) crystallizing the adipic acid from water, preceding or following purification step (d), if crystallization has not been carried out in order to separate the catalyst from the distillation bottoms; and
   (f) recrystallizing the adipic acid from water.

2. The process according to claim 1, wherein the cyclohexane phase obtained in the stage of separation by settling is reintroduced into a cyclohexane oxidation operation.

3. The process according to claim 1, wherein the organic solvent employed in the oxidation of the cyclohexane is an aliphatic carboxylic acid.

4. The process according to claim 1, wherein the catalyst comprises cobalt, manganese or a mixture of cobalt with one or more other metals selected from the group consisting of manganese, chromium, iron, zirconium, hafnium and copper.

5. The process according to claim 1, wherein the stage of distillation of the lower phase is carried out so that the unconverted cyclohexane still present in this lower phase and the solvent are separated from the adipic acid.

6. The process according to claim 1, wherein the distillation stage is carried out at a temperature of 25° C. to 250° C. and under an absolute pressure of between 10 Pa and atmospheric pressure.

7. The process according to claim 1, wherein the distillation stage is completed by an extraction of the distillation bottoms using a water-immiscible organic solvent.

8. The process according to claim 7, wherein the extraction is carried out with an organic solvent selected from the group consisting of aliphatic, cycloaliphatic or aromatic hydrocarbons, aliphatic, cycloaliphatic or aromatic carboxylic acid esters, and ketones.

9. The process according to claim 1, wherein the distillation bottoms obtained at the end of the distillation, which have been subjected, if appropriate, to the extraction operation, are treated, in order to separate the catalyst which they comprise, by a crystallization operation or by an electrodialysis or by passing said solution over an ion-exchange resin or by one or more washing operations with water.

10. The process according to claim 1, wherein the purification is carried out by hydrogenation and/or by treatment with nitric acid and/or by oxidation using molecular oxygen, ozone or hydroperoxide.

11. The process according to claim 10, wherein the purification by hydrogenation is carried out using hydrogen in the presence of a catalyst.

12. The process according to claim 10, wherein the catalyst comprises at least one metal from group VIII of the Periodic Table of Elements, optionally deposited on a solid support.

13. The process according to claim 10, wherein the purification by treatment with nitric acid is carried out with an aqueous solution comprising from 20% to 80% of pure nitric acid by weight per weight of solution.

14. The process according to claim 13, wherein the treatment with nitric acid is carried out by heating the mixture at a temperature of 25° C. to 120° C.

15. The process according to claim 13, wherein the treatment with nitric acid is carried out in the presence of a catalyst comprising one or more cobalt, copper and/or vanadium compounds.

16. The process according to claim 10, wherein the purification by oxidation is carried out with air, air enriched in oxygen or air depleted in oxygen, in the presence of a catalyst.

17. The process according to claim 16, wherein the catalyst is a metal from group VIII of the Periodic Classification of the Elements selected from the group consisting of palladium, platinum, ruthenium, osmium, rhodium and iridium.

18. The process according to claim 10, wherein the purification by oxidation using a hydroperoxide is carried out with hydrogen peroxide.

19. The process according to claim 1, wherein the reducing and/or oxidizing purification treatment is followed by an operation of crystallization and/or of recrystallization of the adipic acid from water.

20. The process according to claim 1, wherein the reducing and/or oxidizing purification treatment is preceded or is followed by a treatment for adsorption of impurities by a finely divided solid.

21. The process according to claim 1, wherein the most volatile compounds are selected from the group consisting of the organic solvent, water, unconverted cyclohexane, cyclohexanone, cyclohexanol, cyclohexyl esters and lactones.

22. The process according to claim 1, wherein step (c) is carried out by crystallization from water, by electrodialysis or by passing over an ion-exchange resin after dissolution of the distillation bottoms in water, by washing with water or by liquid-liquid extraction.

* * * * *